US009470663B2

(12) United States Patent
Li et al.

(10) Patent No.: US 9,470,663 B2
(45) Date of Patent: Oct. 18, 2016

(54) METHOD OF CALIBRATING ULTRASOUND VELOCITY

(71) Applicant: NATIONAL TAIWAN UNIVERSITY, Taipei (TW)

(72) Inventors: Pai-Chi Li, Taipei (TW); Yu-Ming Wei, Taipei (TW)

(73) Assignee: National Taiwan University, Taipei (TW)

(*) Notice: Subject to any disclaimer, the term of this patent is extended or adjusted under 35 U.S.C. 154(b) by 216 days.

(21) Appl. No.: 14/164,566

(22) Filed: Jan. 27, 2014

(65) Prior Publication Data

US 2015/0101390 A1    Apr. 16, 2015

(30) Foreign Application Priority Data

Oct. 11, 2013  (TW) .............................. 102136744 A

(51) Int. Cl.
| | |
|---|---|
| *G01N 29/30* | (2006.01) |
| *A61B 8/00* | (2006.01) |
| *G01N 29/26* | (2006.01) |
| *G01N 29/44* | (2006.01) |
| *A61B 8/08* | (2006.01) |

(52) U.S. Cl.
CPC ................ *G01N 29/30* (2013.01); *A61B 8/58* (2013.01); *G01N 29/262* (2013.01); *G01N 29/4454* (2013.01); *A61B 8/5269* (2013.01)

(58) Field of Classification Search
CPC ........ A61B 8/58; A61B 8/582; A61B 8/585; G01S 7/5205; G01N 29/262; G01N 29/30
USPC ............ 73/602; 116/34 R, 207; 702/39, 103, 702/109; 600/447
See application file for complete search history.

(56) References Cited

U.S. PATENT DOCUMENTS

| | | | | |
|---|---|---|---|---|
| 5,398,538 A | * | 3/1995 | Williams | ............... G01N 29/07 73/1.37 |
| 2003/0196476 A1 | * | 10/2003 | Wood | ...................... G01P 5/245 73/1.82 |
| 2009/0292386 A1 | * | 11/2009 | Cheng | .............. G05B 19/41875 700/109 |
| 2012/0057428 A1 | * | 3/2012 | Specht | ..................... A61B 8/00 367/13 |
| 2013/0173191 A1 | * | 7/2013 | McDonald | ................ H02J 3/00 702/61 |
| 2013/0267849 A1 | * | 10/2013 | Katsuyama | .......... A61B 8/5207 600/443 |
| 2013/0346023 A1 | * | 12/2013 | Novo | ................. G06K 9/00536 702/179 |

* cited by examiner

*Primary Examiner* — Laura Martin
*Assistant Examiner* — Irving A Campbell
(74) *Attorney, Agent, or Firm* — Rosenberg, Klein & Lee

(57) ABSTRACT

A method of calibrating ultrasound velocity is provided, including receiving an ultrasound non-delayed data set; performing a beam-forming process on the ultrasound non-delayed data set with a plurality of velocities to generate a plurality of aperture images; performing a Mean Absolute Percentage Error (MAPE) process to obtain a velocity and two sub-aperture images corresponding to an MAPE value located within an MAPE range; finding a first sub-aperture and a second sub-aperture corresponding to the two sub-aperture images, generating a first aperture image and a second aperture image with corresponding velocity; performing the MAPE process on the first aperture image and the second aperture image to generate an image error corresponding figure having an error curve; finding a trend curve according to the error curve; and finding a lowest point of MAPE value on the trend curve and finding a velocity correspondingly to obtain the calibrated ultrasound velocity.

6 Claims, 7 Drawing Sheets

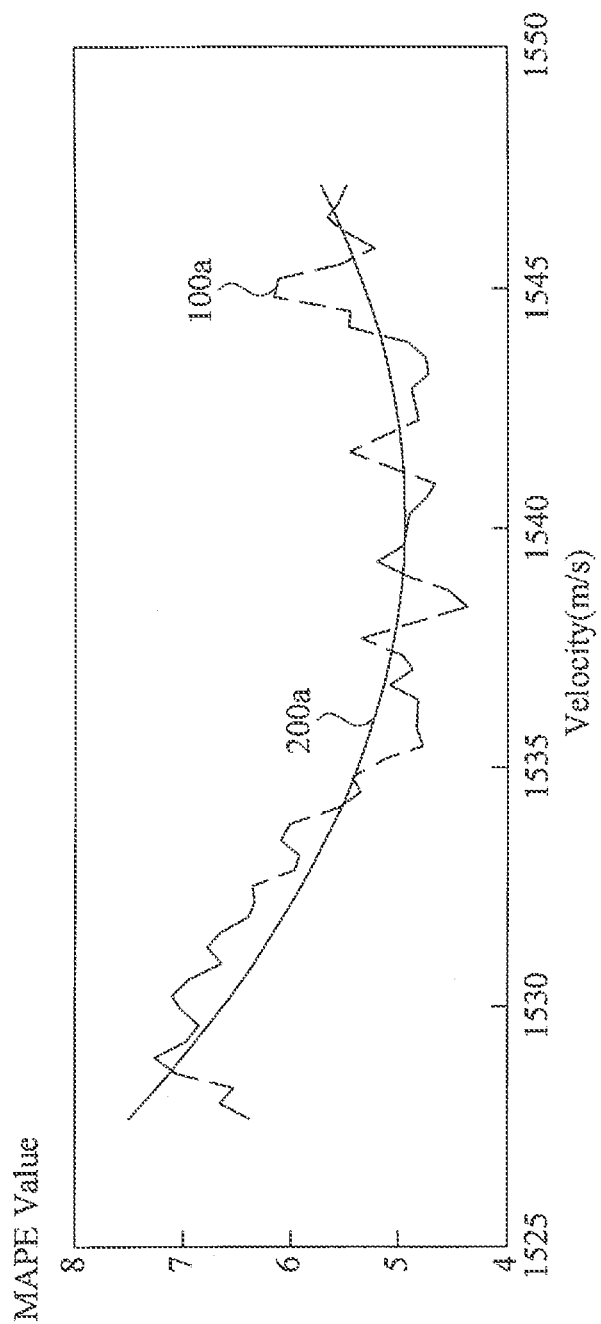

METHOD OF CALIBRATING ULTRASOUND VELOCITY

This application claims the benefits of the Taiwan Patent Application Serial NO. 102136744 filed on Oct. 11, 2013, the subject matter of which is incorporated herein by reference.

BACKGROUND OF THE INVENTION

1. Field of the Invention

The present invention relates to a method of calibrating ultrasound velocity and more particularly, relates to a method of calibrating ultrasound velocity by finding locations of two sub-apertures and performing a Mean Absolute Percentage Error (MAPE) process on two sub-aperture images to obtain calibrated ultrasound velocity.

2. Description

The technique of generating images by means of ultrasound has been widely adopted in biomedical applications. Compared with other medical imaging systems such as X-ray, computed tomography (CT), magnetic resonance imaging (MRI) and nuclear medicine imaging utilized in clinic, ultrasonic imaging has advantages of cost effectiveness, non-invasiveness, no ionizing radiation, real-time imaging capability, high spatial resolution (less than 1 sub-millimeter), portability, flow estimation ability, etc. Thus, ultrasound imaging has been commonly applied to clinical diagnosis in several medical categories.

The principle of ultrasound imaging is to reconstruct an image of an object to be detected with the characteristics of diffraction and reflection of sound waves. Specifically, the principle of ultrasound imaging is to emit sound waves into a human body via a probe; the sound waves interact with all kinds of media in the human body; and users reconstruct images inside the human body according to signals echoed. Recently, ultrasound system of arrays have been widely used in diagnosis and applications, as better image quality can be achieved by adjusting a probe unit for time differences. However, human tissues are not evenly distributed, which affects imaging results. Velocity is an important physical parameter. With mean sounding velocity imaging, problems of bad quality of images due to uneven human tissues are mitigated. Quality of images includes spatial resolution, contrast resolution and even diagnosis of pathological location. In current ultrasound array imaging systems, a default mean velocity (e.g. 1540 m/s) is used for imaging. The difference between the default mean velocity and the actual mean velocity will affect the quality of images and further affect the diagnosis.

Therefore, methods of calibrating velocities have been brought up to obtain a mean velocity which is close to the actual mean velocity in order to improve the quality of images. Current methods of calibration include analyzing the 2D auto-covariance function of images and determining the alignment of delayed data among every unit. In terms of analyzing the 2D auto-covariance function of images, imaging of every velocity is performed in different time; images of every velocity are gathered and a 2D auto-covariance function graph is made according to random image information of focus depth, from which distribution functions are obtained, Full Width Half Maximum (FWHM) of energy (−6 dB) is found and compared with every velocity within the velocity range; a graph showing the trend of the FWHM of energy and every velocity is obtained. Theoretically, the better the resolution is, the smaller the width should be; therefore, it can be observed that the width of the FWHM of energy (−6 dB) will be smaller when being close to the actual velocity. However, data volume of images of every velocity is very heavy and every velocity within the velocity range needs to be compared; as a result, the operation time is too long and not effective.

In terms of determining the alignment of delayed data among every unit, after receiving the echoed ultrasound signals, signals which have been demodulated to fundamental frequency are time-delayed through different velocities; phases of different data are calculated according to every adjacent probe unit; standard deviation is obtained to calculate the alignment; finally, a trend graph showing the relation between the standard deviation and its corresponding velocity range is drawn. Theoretically, in the place close to the mean actual velocity there should be smaller standard deviation and better alignment; on the contrary, places farther from the mean actual velocity have greater standard deviation and worse alignment. However, whether the data are aligned is determined by means of velocity iteration; but practically when there is a small deviation among the alignment of data, the accuracy of following data will be affected, which takes longer data operation time and is inaccurate, and further affects its application in clinical diagnosis.

SUMMARY OF THE INVENTION

In prior art, methods of calibrating ultrasound velocity have problems of longer operation time and inaccurate calibration of velocity, which further affects the application in clinical diagnosis. Thus, a method of calibrating ultrasound velocity is provided according to embodiments of the present invention. The method includes parallel ways for imaging in every velocity and finding locations of two sub-apertures, parallel ways for imaging at the same time with the two sub-apertures in every velocity, and calibrating the ultrasound velocity by a Mean Absolute Percentage Error (MAPE) process to decrease the operation time and increase the accuracy.

A method of calibrating ultrasound velocity to obtain a calibrated ultrasound velocity for imaging is provided according to embodiments of the present invention, the method including following steps: (a) receiving an ultrasound non-delayed data set; (b) performing a beam-forming process on the ultrasound non-delayed data set with a plurality of velocities from a plurality of sub-apertures of a probe to generate a plurality of sub-aperture images; (c) performing an MAPE process on the aperture images to obtain MAPE values, obtaining an intermediate calibration velocity and two first calibration sub-aperture images corresponding to an MAPE value located within an MAPE range; (d) finding a first sub-aperture and a second sub-aperture corresponding to the two sub-aperture images, performing the beam-forming process on the ultrasound non-delayed data set with the first calibration velocity to generate a first aperture image corresponding to the first sub-aperture and a second aperture image corresponding to the second sub-aperture; (e) performing the MAPE process on the first aperture image and the second aperture image to generate an image error corresponding figure having an error curve; (f) finding a trend curve according to the error curve; and (g) finding a lowest point on the trend curve and finding a velocity corresponding to the lowest point to obtain the calibrated ultrasound velocity, wherein the lowest point on the trend curve shows the lowest MAPE value.

According to a preferable embodiment of the present invention, in step (b), the probe is selected from the group of a one-dimensional array probe and a two-dimensional array probe; the first sub-aperture is located in an aperture in the center of the probe and the second sub-aperture is located in an aperture around the probe. The MAPE range is from 1.5% to 3%; and the first sub-aperture includes a first aperture size and the second sub-aperture includes a second aperture size; the second sub-aperture and the first sub-aperture have a distance in-between; step (d) further includes finding the first aperture size, the second aperture size and the distance.

According to the preferable embodiment of the present invention, in step (e), the first aperture image includes a plurality of first pixel values and the second aperture image includes a plurality of second pixel values; the first pixel values and the second pixel values correspondingly have a first beam value and a second beam value; the first pixel values are defined as $M_{ij}$ (which is an array of first pixel values with indices i and j ranging from 1 to $N_x$ and from 1 to $N_y$, respectively), the second pixel values are defined as $S_{ij}$ (which is an array of second pixel values with indices i and j ranging from 1 to $N_x$ and from 1 to $N_y$, respectively), the first beam value is defined as $N_x$, the second beam value is defined as $N_y$, the MAPE value is defined as d. Thus, the first sub-aperture is mathematical construct of beam forming containing a view of a first sub-aperture image from the perspective of the first sub-aperture and the second sub-aperture is a mathematical construct of beam forming containing a view a second sub-aperture image from the perspective of the second sub-aperture offset from the first sub-aperture. The MAPE value is given by calculating the Mean of the Absolute value of the Percentage Error for each pixel value pair given by equation (1). The value from standard non-array percentage error calculations is commonly multiplied by 100 and represented with a percentage sign (%).

$$d = \frac{\sum_{i=1}^{Nx} \sum_{j=1}^{Ny} \left| \frac{M_{ij} - S_{ij}}{M_{ij}} \right|}{(N_x \cdot N_y)} \quad (1)$$

According to embodiments of the present invention, the method provides a calibration of an ultrasonic probe to utilize a velocity among various velocities in a parallel manner; therefore, the operation time is decreased and the accuracy is improved so that ultrasound imaging with the calibrated velocity according to embodiments of the present invention has better images. Thus, the diagnosis is more accurate and more effective.

BRIEF DESCRIPTION OF THE DRAWINGS

Other features and advantages of this invention will become more apparent in the following detailed description of the preferred embodiments of this invention, with reference to the accompanying drawings.

FIG. 4A is a schematic view showing an image error corresponding figure according to an embodiment of the present invention.

DETAILED DESCRIPTION OF THE PREFERRED EMBODIMENT

The present invention relates to a method of calibrating ultrasound velocity. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
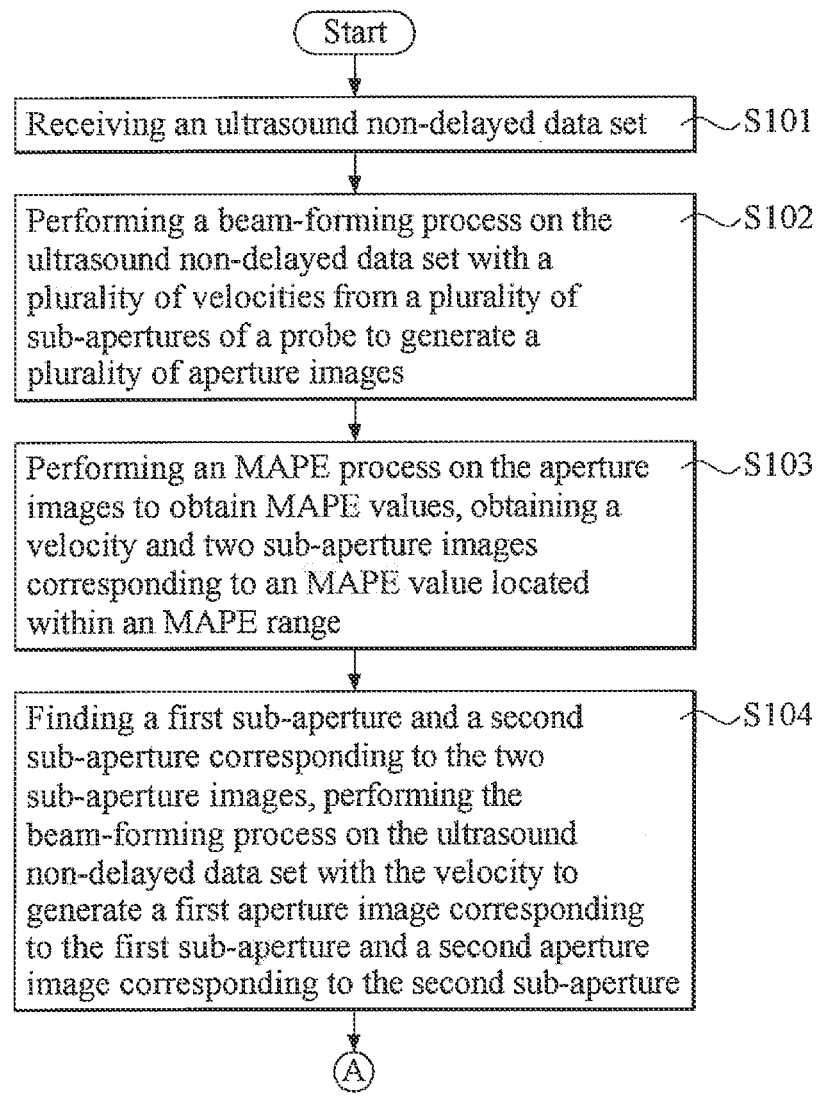
FIG. 1 and FIG. 1A are flow charts showing a method of calibrating ultrasound velocity according to a preferable embodiment of the present invention.
Figure 1A:
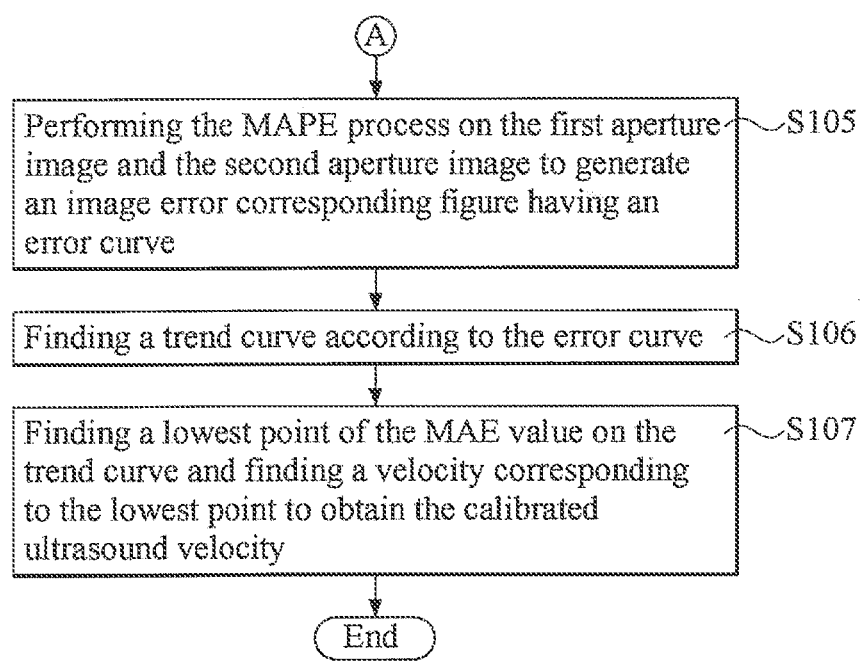
Figure 2:
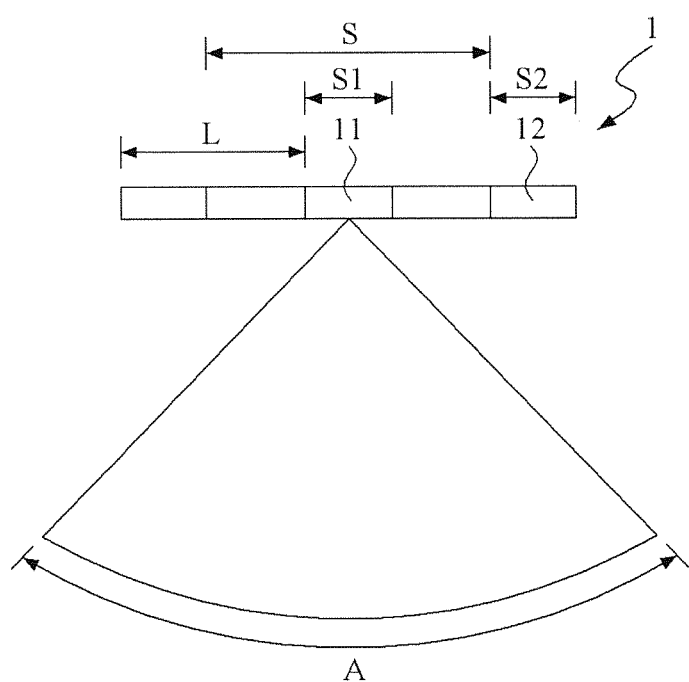
FIG. 2 is a schematic view showing a probe of the preferable embodiment of the present invention.
Figure 3:
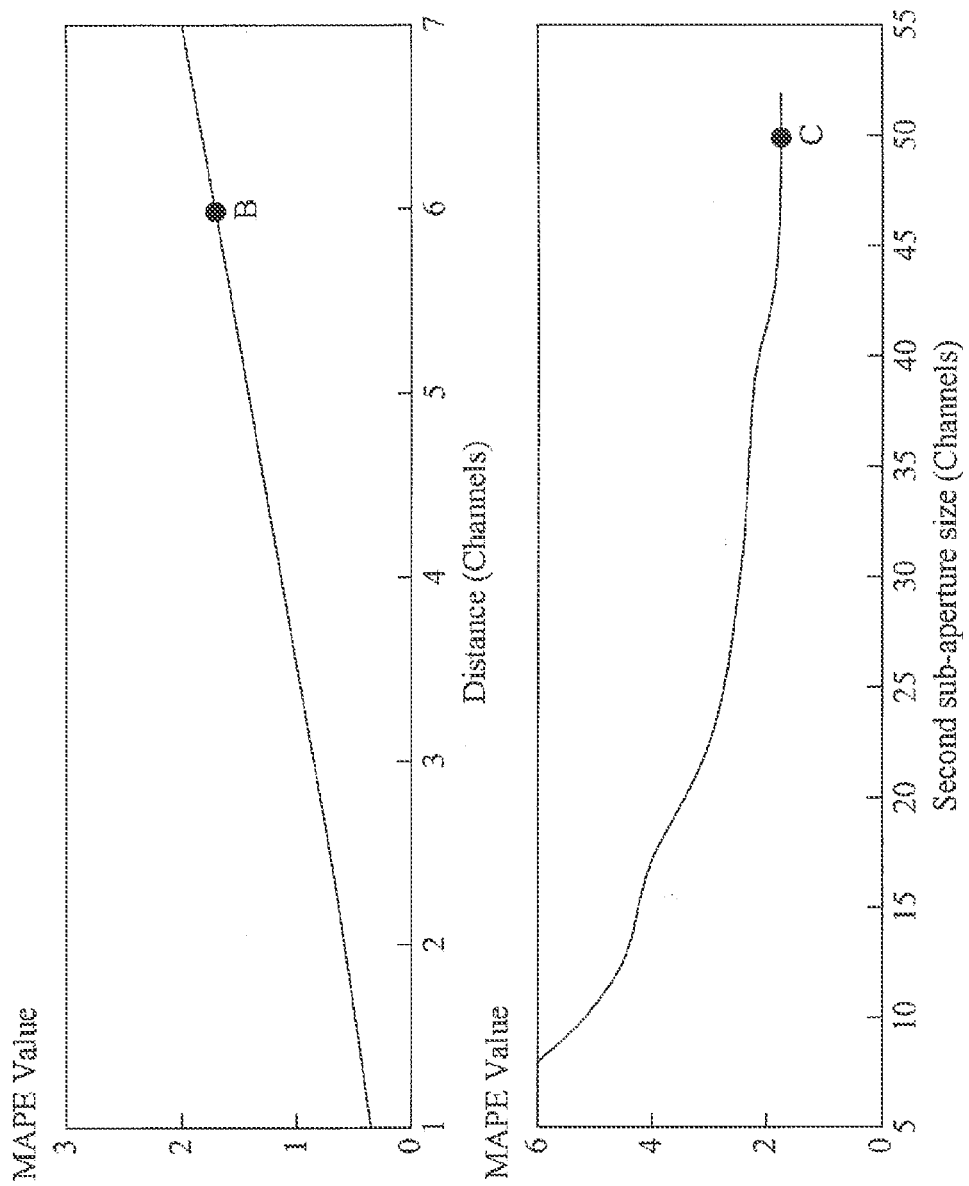
FIG. 3 is a schematic view showing a relation among MAPE values, distances between a first and a second sub-aperture, and sizes of the second sub-aperture according to the preferable embodiment of the present invention.
Figure 4:
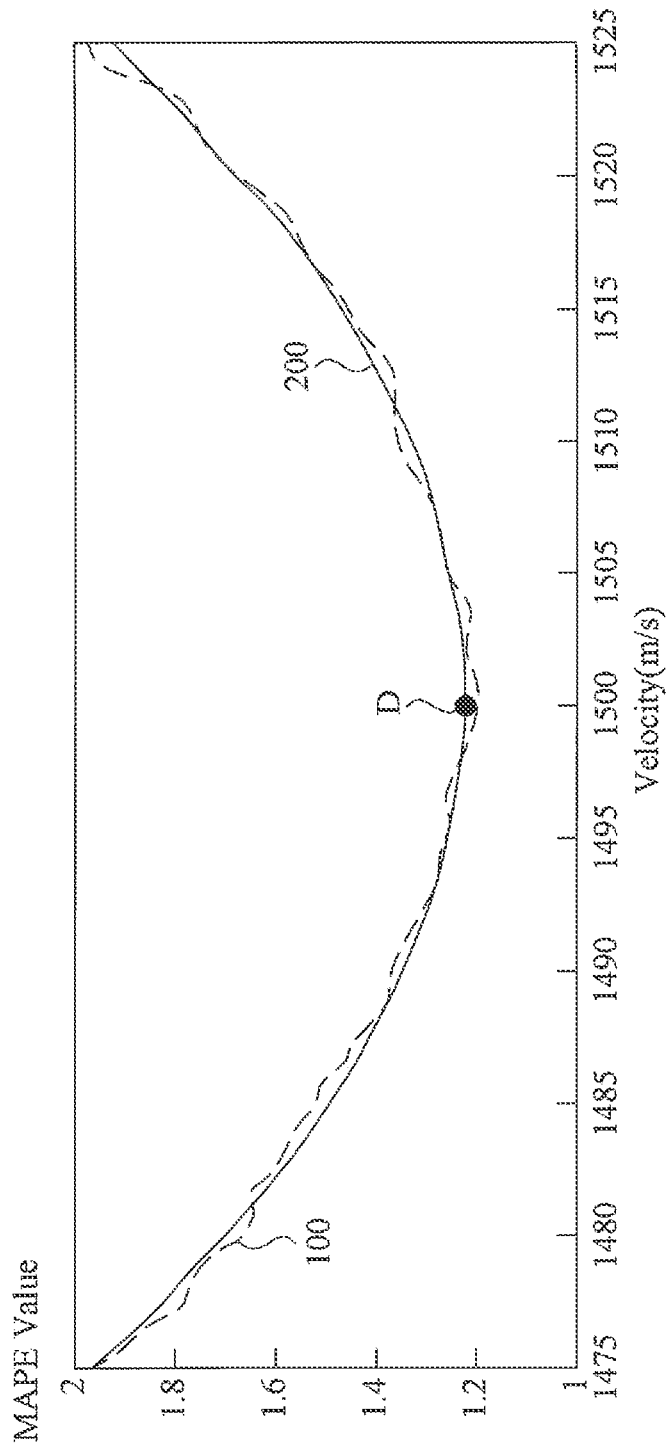
FIG. 4 is a schematic view showing an image error corresponding figure according to the preferable embodiment of the present invention.

Refer to FIG. 1 to FIG. 4. FIG. 1 and FIG. 1A are flow charts showing a method of calibrating ultrasound velocity according to a preferable embodiment of the present invention. FIG. 2 is a schematic view showing a probe of the preferable embodiment of the present invention. FIG. 3 is a schematic view showing a relation among MAPE values, distances between a first and a second sub-aperture, and sizes of the second sub-aperture according to the preferable embodiment of the present invention. FIG. 4 is a schematic view showing an image error corresponding figure according to the preferable embodiment of the present invention.

According to the drawings, a method of calibrating ultrasound velocity to obtain a calibrated ultrasound velocity for imaging is provided according to embodiments of the present invention, the method including following steps:

S101: receiving an ultrasound non-delayed data set;

S102: performing a beam-forming process on the ultrasound non-delayed data set with a plurality of velocities from a plurality of sub-apertures of a probe to generate a plurality of aperture images;

S103: performing an MAPE process on the aperture images to obtain MAPE values, obtaining a first calibration velocity and choosing two of the sub-aperture images corresponding to an MAPE value located within an MAPE range;

S104: selecting a first sub-aperture and a second sub-aperture corresponding to the two sub-aperture images, performing the beam-forming process on the ultrasound non-delayed data set with the first calibration velocity to generate a first aperture image corresponding to the first sub-aperture and a second aperture image corresponding to the second sub-aperture;

S105: performing the MAPE process on the first aperture image and the second aperture image to generate an image error figure having an error curve;

S106: finding a trend curve according to the error curve; and

S107: finding a lowest point on the trend curve and finding a velocity corresponding to the lowest point to obtain the calibrated ultrasound velocity, wherein the lowest point on the trend curve shows the lowest MAPE value.

Step S101 is to receive a data set formed by echoed ultrasound and the data set has neither been in a delayed process nor in an image process.

In step S102, according to FIG. 2, the probe 1 is a one-array probe according to the preferable embodiment of the present invention and the probe 1 includes five sub-apertures (not all five sub-apertures being enumerated). In other embodiments of the present invention, the numbers of sub-apertures of the probe 1 are not limited to five. According to the preferable embodiment of the present invention, a first sub-aperture 11 and a second sub-aperture 12 are taken as examples out of the five sub-apertures, wherein the first sub-aperture 11 is located in the central sub-aperture of the probe 1 and the second sub-aperture 12 is located in the far right and the far left sub-aperture around the probe 1. (In other embodiments of the present invention, the second sub-aperture 12 is located in the far right or the far left sub-aperture.)

Specifically, the method according to the preferable embodiment of the present invention selects which two sub-apertures to be utilized for calibrating the ultrasound velocity among the sub-apertures. The ultrasound non-delayed data set received in S101 is performed with the beam-forming process (according to the preferable embodiment, the beam-forming process includes performing with 300 beams within a beam-forming range A and determining images according to 20 beams in the center) with a plurality of velocities (e.g. every velocity from 1474 m/s to 1550 m/s). Beam-forming process is a common technique and is not mentioned redundantly here. Since every sub-aperture is performed with the beam-forming process, every sub-aperture is resolved into sub-aperture images (not shown) corresponding to the velocities. For example, when the ultrasound non-delayed data set is performed with the beam-forming process with 10 kinds of velocities, the five sub-apertures of the preferable embodiment of the present invention respectively have 10 aperture images. In other words, each of the 10 velocities has a corresponding total aperture image with each of the 10 aperture images having 5 sub-apertures that correspond to 5 sub-aperture images. Of the 5 sub-apertures images for each velocity, 2 sub-apertures images are used for calculating the MAPE value for each velocity.

In step S103, when the velocities are set between 1475 m/s to 1550 m/s, utilizing the aperture images formed by the beam forming process using the two sub-apertures, MAPE process is used to select a corresponding velocity (e.g. 1500 m/s) from the velocity range and two sub-aperture images according to an MAPE value located within an MAPE range.

For example, according to FIG. 3, the MAPE range is from 1.5% to 3% according to the preferable embodiment of the present invention. The MAPE value calculated according to the two aperture images is within the aperture image of the MAPE range. Therefore, in step S103, a first aperture image and a second aperture image are selected and found to be accurate within the MAPE range.

In step S104, since the first aperture image and the second aperture image are found in step S103, two sub-apertures corresponding to the two aperture images can be further found, wherein the first sub-aperture 11 corresponds to the first aperture image and the second sub-aperture 12 corresponds to the second aperture image 12. The first sub-aperture 11 includes a first aperture size S1 and the second sub-aperture 12 includes a second aperture size S2; the aperture size formed by the first sub-aperture 11 and sub-apertures in its two sides is S. The most sided (the far left in FIG. 2) of the second sub-aperture 12 and the first sub-aperture 11 have a distance L in-between. In step S104, above-mentioned parameters are selected.

Furthermore, according to FIG. 3, the first sub-aperture size S1 is 50 channels; from a sampling point B, the distance L is 6 channels; and from a sampling point C, the second sub-aperture size S2 is 50 channels. Thus, the parameters are decided in this step.

After the parameters are decided, the ultrasound non-delayed data set is again performed with the beam-forming process in the corresponding velocity 1500 m/s so as to generate a new first sub-aperture image and sub-second aperture image.

In step S105, the MAPE process is performed on the first sub-aperture image and the second sub-aperture image to generate an image error corresponding figure having an error curve 100 as shown in FIG. 4.

Specifically, the first sub-aperture image includes a plurality of first pixel values and the second sub-aperture image includes a plurality of second pixel values. The first pixel values and the second pixel values correspondingly have a first beam value and a second beam value. The first pixel values are defined as $M_{ij}$, the second pixel values are defined as $S_{ij}$, the first beam value is defined as $N_x$, the second beam value is defined as $N_y$, the MAPE value is defined as d. Value of every point on the error curve 100 is calculated by the previously recited equation (1).

$$d = \frac{\sum_{i=1}^{Nx} \sum_{j=1}^{Ny} \left| \frac{M_{ij} - S_{ij}}{M_{ij}} \right|}{(N_x \cdot N_y)} \quad (1)$$

In step S106, a trend curve 200 is found according to the error curve 100. In step S107, a lowest point D of the MAPE value on the trend curve 200 and the velocity corresponding to the lowest point D are found to obtain the calibrated ultrasound velocity. Specifically, according to the preferable embodiment of the present invention, the velocity of 1500 m/s is found as the corresponding velocity to the lowest point D of the MAPE value; thus, the velocity of 1500 m/s is the calibrated ultrasound velocity. A processer including a CPU or a GPU can execute step S101 to step S107.

Figure 4B:
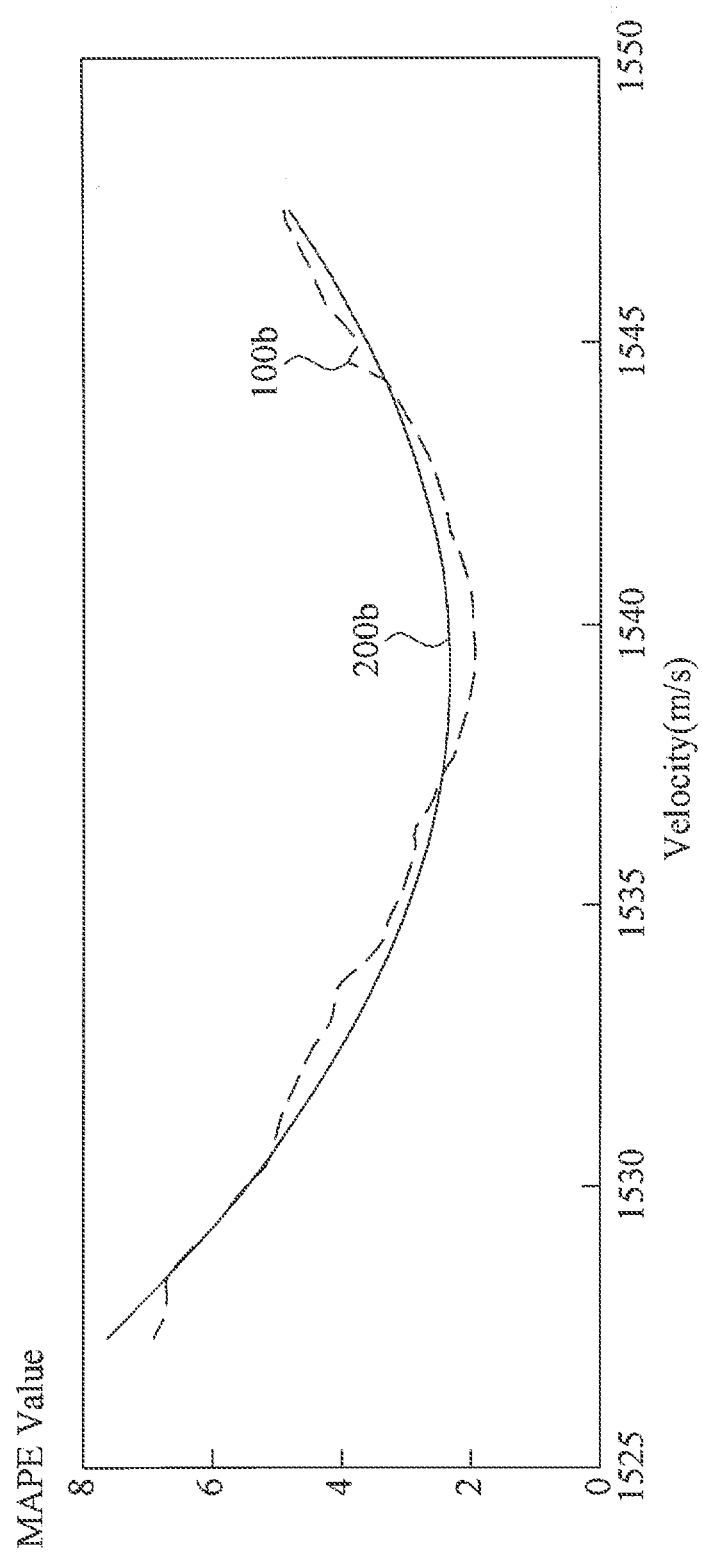
FIG. 4B is a schematic view showing an image error corresponding figure according to another embodiment of the present invention.

Refer to FIG. 4A and FIG. 4B. FIG. 4A is a schematic view showing an image error corresponding figure according to an embodiment of the present invention. FIG. 4B is a schematic view showing an image error corresponding figure according to another embodiment of the present invention. According to FIG. 4A, the first sub-aperture size is 80 channels; the distance is 24 channels; according to the trend curve 200a found by its error curve 100a, the calibrated ultrasound velocity is 1540 m/s. According to FIG. 4B, the first sub-aperture size is 100 channels; the distance is 14 channels; according to the trend curve 200b found by its error curve 100b, the calibrated ultrasound velocity is also 1540 m/s.

In conclusion, according to embodiments of the present invention, the method calibrates better velocity among various velocities in a parallel way; therefore, the operation time is decreased and the accuracy is improved so that ultrasound imaging with the calibrated velocity according to embodiments of the present invention has better images. Thus, the diagnosis is more accurate and more effective.

While the present invention has been particularly shown and described with reference to a preferred embodiment, it will be understood by those skilled in the art that various changes in form and detail may be without departing from the spirit and scope of the present invention.

What is claimed is:

1. A method of calibrating ultrasound velocity to obtain a calibrated ultrasound velocity for imaging, the method comprising the following steps:
   (a) receiving an ultrasound non-delayed data set;
   (b) performing a beam-forming process on the ultrasound non-delayed data set with a plurality of velocities defining a plurality of sub-apertures of a probe to generate a plurality of sub-aperture images;
   (c) performing a Mean Absolute Percentage Error (MAPE) process on the sub-aperture images to obtain MAPE values defining a MAPE range, obtaining an intermediate calibration velocity and two calibration sub-aperture images corresponding to a pre-selected MAPE value located within said MAPE range;
   (d) selecting a first sub-aperture and a second sub-aperture corresponding to the two calibration sub-aperture images, performing the beam-forming process on the ultrasound non-delayed data set with the intermediate calibration velocity to generate a first aperture image corresponding to the first sub-aperture and a second aperture image corresponding to the second sub-aperture;
   (e) utilizing the first aperture image and the second aperture image to generate an image error figure having an error curve;
   (f) finding a trend curve according to the error curve; and
   (g) finding a lowest point on the trend curve and finding a velocity corresponding to the lowest point to obtain the calibrated ultrasound velocity, wherein the lowest point on the trend curve shows the lowest MAPE value.

2. The method according to claim 1, wherein in step (b), the probe is selected from the group of a one-dimensional array probe and a two-dimensional array probe.

3. The method according to claim 1, wherein the first sub-aperture is located in an aperture in the center of the probe and the second sub-aperture is located in an aperture around the probe.

4. The method according to claim 1, wherein in step (c), the MAPE range is from 1.5% to 3%.

5. The method according to claim 1, wherein the first sub-aperture includes a first aperture size and the second sub-aperture includes a second aperture size; the second sub-aperture and the first sub-aperture have a distance in-between; step (d) further includes finding the first aperture size, the second aperture size and the distance.

6. The method according to claim 1, wherein in step (e), the first aperture image includes a plurality of first pixel values and the second aperture image includes a plurality of second pixel values; the first pixel values and the second pixel values correspondingly have a first beam value and a second beam value; the first pixel values are defined as $M_{ij}$, the second pixel values are defined as $S_{ij}$, the first beam value is defined as $N_x$, the second beam value is defined as $N_y$, the MAPE value is defined as d, and $$d = \frac{\sum_{i=1}^{N_x} \sum_{j=1}^{N_y} \left| \frac{M_{ij} - S_{ij}}{M_{ij}} \right|}{(N_x \cdot N_y)}.$$

* * * * *